(12) United States Patent
Albers et al.

(10) Patent No.: US 7,268,103 B2
(45) Date of Patent: Sep. 11, 2007

(54) USE OF ALKOXYLATED HYDROXYCARBOXYLIC ACID ESTERS FOR SOLUBILIZING PERFUME OILS IN WATER

(75) Inventors: Thomas Albers, Duesseldorf (DE); Ansgar Behler, Bottrop (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 11/263,646

(22) Filed: Oct. 31, 2005

(65) Prior Publication Data

US 2006/0128577 A1  Jun. 15, 2006

(30) Foreign Application Priority Data

Nov. 5, 2004  (DE)  ............ 10 2004 054 036

(51) Int. Cl.
*C11D 3/50* (2006.01)

(52) U.S. Cl. ............................ 510/101; 510/505

(58) Field of Classification Search ............. 510/101, 510/505
See application file for complete search history.

(56) References Cited

U.S. PATENT DOCUMENTS 6,413,527 B1 * 7/2002 Simonnet et al. .......... 424/401

FOREIGN PATENT DOCUMENTS

| DE | 4025925 | * | 2/1992 |
|----|---------|---|--------|
| EP | 0 199 131 | | 10/1986 |
| EP | 199131 | * | 10/1986 |
| EP | 282289 | * | 9/1988 |
| EP | 852944 | * | 7/1998 |
| EP | 1099748 | * | 11/2000 |
| WO | WO94/10970 | | 5/1994 |
| WO | WO 02/34216 | * | 5/2002 |
| WO | WO 2004/056741 | | 7/2004 |

* cited by examiner

*Primary Examiner*—John R. Hardee
(74) *Attorney, Agent, or Firm*—John F. Daniels; Richard A. Elder

(57) ABSTRACT

The invention relates to the use of esters of hydroxycarboxylic acids with alkoxylated fatty alcohols as solubilizers for perfume oils in water. These esters not only have a strong solubilizing effect on water-insoluble perfume oils, they are also capable of dispersing calcium ions.

13 Claims, No Drawings

USE OF ALKOXYLATED HYDROXYCARBOXYLIC ACID ESTERS FOR SOLUBILIZING PERFUME OILS IN WATER

CROSS-REFERENCE TO RELATED APPLICATIONS

This application claims priority under 35 USC §119 from German Application No. 10 2004 054 036.5, filed on Nov. 5, 2004.

STATEMENT REGARDING FEDERALLY SPONSORED RESEARCH OR DEVELOPMENT

Not Applicable.

BACKGROUND OF THE INVENTION

This invention relates to the use of alkoxylated hydroxycarboxylic acid esters as solubilizers for perfume oils in water. These solubilizers may be used, for example, in cleaning compositions.

Besides the actual cleaning ingredients, increasingly more cleaning compositions both for institutional and for domestic use also contain perfume oils to give the products a pleasant fragrance which is intended to last for as long as possible in use. The cleaning compositions in question include, in particular, products for cleaning toilets, such as for example toilet blocks or toilet gels. It has been found that the use of large amounts of perfume oils leads to problems because they do not always dissolve sufficiently on contact with water.

Accordingly, there is a need for such perfume oils—which are generally insoluble in water—to be dissolved or dispersed in water with the aid of suitable auxiliaries known as solubilizers. According to WO 94/10970 A1, monoalkyl citrates whose alkyl groups must contain 7 to 10 carbon atoms are suitable for this purpose. These monoalkyl citrates are suitable for solubilizing perfume oils in so-called personal care and household products. However, there is a constant demand for other suitable and improved solubilizers. In particular, the solubilizers are expected to perform an additional function. It has been found that certain hydroxycarboxylic acid ester derivatives can satisfy this requirement.

The present invention relates to the use of esters of hydroxycarboxylic acids with alkoxylated fatty alcohols as solubilizers for perfume oils in water.

Solubilizers are substances which, through their presence, make other compounds, which are largely insoluble in a certain solvent (in the present case water), soluble or emulsifiable in that solvent.

Alkoxylated esters of hydroxycarboxylic acids are already known and are described, for example, in EP-A2-0 199 131. This document discloses low-ethoxylated citric acid alkyl esters as water-soluble surfactants, more particularly for use in cosmetic formulations. It does not state that the ethoxylated citric acid esters could be suitable for solubilizing perfume oils in water. The production of the esters of hydroxycarboxylic acids with alkoxylated fatty alcohols used in accordance with the invention is described, for example, in WO 2004/056741-A1. To this end, ethoxylated fatty alcohols are introduced with citric acid into a stirred reactor with a water separator and then heated to temperatures of up to 160° C. On completion of the reaction, the mixture is cooled and the ester is obtained by distillation.

BRIEF SUMMARY OF THE INVENTION

The present invention relates to the use of esters of hydroxycarboxylic acids with alkoxylated fatty alcohols as solubilizers for perfume oils in water. These solubilizers may be used, for example, to facilitate the addition of perfume oils to cleaning compositions.

DETAILED DESCRIPTION OF THE INVENTION

The hydroxycarboxylic acids used to make the ester solubilizers in accordance with the invention are preferably so-called fruit acids. Fruit acids is the collective name for organic acids often found in fruit which, besides aroma development and antimicrobial activity, show a number of other desirable effects in foods. According to the invention, the fruit acids are preferably selected from the group consisting of citric acid, lactic acid, malic acid, tartaric acid and gluconic acid. Today, these fruit acids are mostly obtained by biotechnological methods. For example, citric acid can be obtained from molasses by fermentation with *Aspergillus nigra* while gluconic acid can be obtained by enzymatic oxidation of glucose. A preferred hydroxycarboxylic acid for the purposes of the present technical teaching is citric acid. Oligo- or polycarboxylic acids are also preferably used. In other words, preferred carboxylic acids contain at least 2 carboxylic acid functions—COOH in the molecule. However, hydroxycarboxylic acids containing 3 to 6 carboxylic acid groups in the molecule may also be used. A hydroxycarboxylic acid in the present context means that, besides at least one carboxylic acid group, at least one free hydroxyl group must be present in the molecule.

As described above, the hydroxycarboxylic acids are preferably reacted with alkoxylated fatty alcohols to form the actually effective ester compounds. The alkoxylated fatty alcohols preferably correspond to general formula (I):

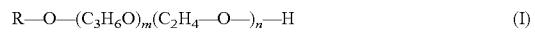

$$R-O-(C_3H_6O)_m(C_2H_4-O-)_n-H \qquad (I)$$

in which the indices n and m independently of one another stand for 0 or for a number of 1 to 10, with the proviso that the sum of n and m must be at least 1, and the substituent R is a saturated, unsaturated, branched or unbranched $C_{8-22}$ alkyl group. Alkoxylated fatty alcohols of formula (I), where m is 0 and n is a number of 1 to 10, preferably 2 to 8 and more particularly 4 to 7, are preferably used. Other preferred fatty alcohols of formula (I) are those in which R represents saturated, unbranched alkyl chains containing 8 to 22 and preferably 12 to 18 carbon atoms. The alkoxylates used may be both ethoxylated and purely propoxylated compounds. It can be of advantage to use ethoxylated and propoxylated compounds of formula (I) for the production of the esters according to the invention.

Compounds of formula (I) where m is 0 and n is a number of 1 to 10, preferably 2 to 8 and more particularly 5 to 7 are preferably selected. If purely propoxylated compounds are selected, then compounds of formula (I) where n is 0 and m is a number of 1 to 6, preferably 1 to 4 and more particularly 2 to 4 are preferred. In the case of ethoxylated and propoxylated isomers of formula (I), values of 1 to 2 for m and 4 to 8 for n are preferred. The sequence of the alkoxide groups in formula (I) is arbitrary. In other words, both random sequences of ethylene and propylene oxide groups are encompassed by the general formula, as are products which contain these alkoxide groups in blocks. In no way should formula (I) be interpreted to mean that a sequence of propylene oxides and then ethylene oxides should be present. However, compounds of formula (I) where first a propylene oxide block and then an ethylene oxide block follow one another are preferred.

The hydroxycarboxylic acid esters used in accordance with the invention are surfactants which, preferably, still contain a free carboxyl group. Accordingly, the esters may be acidic esters or neutralization products thereof. They are then preferably present in the form of alkali metal, alkaline earth metal, ammonium, alkylammonium, alkylammonium and/or glucammonium salts.

The esters themselves are preferably derived from ethoxylated fatty alcohols corresponding to formula (I) which are reacted with the hydroxycarboxylic acids. Esters prepared by mixing alkoxylated, preferably ethoxylated, fatty alcohols of general formula (I) with fatty alcohols corresponding to the following general formula:

R—OH                                    (II)

with the hydroxycarboxylic acids may also be used in accordance with the invention. In formula (II), R is a saturated, unsaturated, branched or unbranched alkyl group containing 8 to 22 carbon atoms. In a preferred embodiment, the ratio by weight between the alcohols (II) and the ethoxylated alcohols (I) is in the range from 10:1 to 1:10. In a particularly preferred embodiment, the alcohols of formulae (II) and (I) are reacted in a ratio by weight of 10:1 to 1:1 and more particularly, 9:1 to 1:1, preferably 4:1 to 1:1 and, more especially, 1:1.

The esters according to the invention are preferably polyesters where several carboxyl functions are esterified. For production-related reasons, mixtures of the esters are typically present, the reaction mixtures predominantly containing monoesters. In a preferred embodiment, the reaction mixture contains 75 to 95% by weight monoesters, 25 to 5% by weight diesters and small amounts (0.01 to 5% by weight) triesters, based on the esterified component.

The present invention also relates to mixtures of isomeric compounds corresponding to general formula (III):

in which R', R", R'" represent a hydrogen atom and/or a $C_{6-22}$ alkyl group and/or an ethoxylated $C_{6-22}$ alkyl group, the ethoxylated alkyl groups containing between 2 and 20 parts ethylene oxide per alkyl group, with the provisos that at least one of the substituents R', R" and R'" represents such an ethoxylated alkyl group and the total number of ethylene oxide units per ester molecule is limited to 20.

The mixtures contain mono-, di- and triesters alongside one another, mono- and diesters preferably being present alongside one another in a ratio of 3:1 to 10:1. The percentage of free citric acid may be up to 20%, based on the mixtures. However, the mixtures preferably contain less free citric acid, preferably less than 10% by weight, more preferably less than 7% by weight and most preferably less than 5% by weight. Ideally, the mixtures are actually free from citric acid.

The present invention relates to the use of the above-described hydroxycarboxylic acid derivatives for solubilizing perfumes in water. The perfumes may be both solid and liquid at room temperature (21° C.), liquid perfumes or perfume oils being preferred. Compounds which are poorly soluble or insoluble in water are preferably used. Poor solubility means, for example, that only at most 5% by weight, preferably at most 1% by weight or up to at most 0.1% by weight of the perfume dissolves in water at 21° C. Mixtures of natural and synthetic perfumes, for example, are mentioned as perfume oils. Natural perfumes include the extracts of blossoms, stems and leaves, fruits, fruit peel, roots, woods, herbs and grasses, needles and branches, resins and balsams. Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, p-tert.butyl cyclohexylacetate, linalyl acetate, phenyl ethyl acetate, linalyl benzoate, benzyl formate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labdanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romilat, irotyl and floramat.

According to the invention, it is particularly preferred to use the above-described alkoxylated hydroxycarboxylic acid esters with perfume oils or perfumes based on unsaturated aliphatic aldehydes, preferably octyl aldehyde. Another preferred perfume is cumene. Orange oil and/or lemon oil terpene are also preferred perfumes in the context of the present invention. The perfume oils may be solubilized in water either individually or in the form of mixtures with one another using the hydroxycarboxylic acid described above. However, the perfumes may first be dissolved in a non-aqueous solvent, for example an alcohol, such as ethanol or propanol, and the dissolved perfume may then be solubilized with the hydroxycarboxylic acids according to the invention.

The esters of hydroxycarboxylic acids with alkoxylated fatty alcohols used in accordance with the invention are suitable as solubilizers for perfume oils in water. Surprisingly, however, they perform an additional function, i.e. they have a complexing effect, particularly on calcium ions. The alkoxylated hydroxycarboxylic acids used in accordance with the invention thus combine two product properties in one substance: the use according to the invention makes it unnecessary to use such complexing agents as, for example, phosphonates, free fruit acids, strong acids or, for example, EDTA in addition to the solubilizers.

Another advantage of the present invention is that, in the use according to the invention, the residue is dispersed in the cleaning liquor. By contrast, residues which float on the liquid surface occur where conventional complexing agents are used. Accordingly, by using the alkoxylated hydroxycarboxylic acid in accordance with the invention, lime residues can be better dispersed with the cleaning solution.

The alkoxylated esters of hydroxycarboxylic acids according to the invention may be used on their own, but are preferably used in combination with other ingredients, for example, and preferably in cleaning compositions. Other ingredients may be typical components known to the expert for such applications, preferably other surfactants from the group of nonionic, anionic, cationic and/or amphoteric surfactants. Nonionic surfactants in the context of the invention may be alkoxylated alcohols, such as polyglycol ethers, fatty alcohol polyglycol ethers, alkylphenol polyglycol ethers, end-capped polyglycol ethers, mixed ethers, hydroxy mixed ethers, alkoxylated carboxylic acid esters, amine oxides and alkyl polyglycosides. Ethylene oxide/propylene oxide block polymers and fatty acid alkanolamides and fatty acid polyglycol ethers may also be used. In a particularly preferred embodiment, alkyl polyglycosides are present as nonionic surfactants in the compositions according to the invention either on their own or in combination with other nonionic surfactants.

Alkyl polyglycosides are known nonionic surfactants which correspond to the formula RO-[G]$_p$, where R is an alkyl and/or alkenyl group containing 6 to 22 carbon atoms, G is a sugar unit containing 5 or 6 carbon atoms and p is a number of 1 to 10. They may be obtained by the relevant methods of preparative organic chemistry. The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides. The index p in general formula (I) indicates the degree of oligomerization (DP), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational perspective. The alkyl or alkenyl group R may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred. In addition, the alkyl or alkenyl group R may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

The compositions according to the invention may contain the nonionic surfactants, preferably the alkyl polyglycosides either on their own or in admixture with amine oxides, as sole surfactant. However, the compositions according to the invention may additionally contain anionic and preferably cationic and/or amphoteric or zwitterionic surfactants. Anionic surfactants, for example aliphatic sulfates, such as fatty alcohol sulfates, fatty alcohol ether sulfates, fatty acid polyglycol ester sulfates, dialkyl ether sulfates, monoglyceride sulfates, and aliphatic sulfonates, such as alkanesulfonates, olefin sulfonates, ether sulfonates, n-alkyl ether sulfonates, ester sulfonates, and lignin sulfonates may be present in small quantities. Preferred anionic surfactants are fatty alcohol sulfates, fatty alcohol ether sulfates and/or fatty acid polyglycol ester sulfates. However, since the anionic surfactants interact with the cationic polymers as thickeners, precipitations can occur in particular with strong anionic surfactants, above all even when the quantity of anionic surfactants exceeds 10% by weight, based on the total quantity of surfactants. In order to guarantee clear compositions, it is particularly preferred in accordance with the invention if the compositions according to the invention contain only small amounts of anionic surfactants, i.e. less than 2.5% by weight, preferably less than 1.5% by weight anionic surfactants, and, better still, no anionic surfactants at all. Accordingly, alkoxylated fatty alcohol hydroxycarboxylic acid esters in the context of the present invention are preferably used in compositions which contain little, if any, anionic surfactant.

The compositions according to the invention may contain quaternary ammonium compounds and esterquats, more particularly quaternized fatty acid trialkanolamine ester salts, as cationic surfactants. In a particularly preferred embodiment, these surfactants may be used in combination with amine oxides and/or alkyl glycosides.

Builders and/or other ingredients, for example disinfectants, biocides, dyes, thickeners and preferably polymeric thickeners, pH adjusters, nonaqueous solvents, such as preferably ethanol, propanol or ethylene glycol and derivatives thereof, may also be present. In the case of foam cleaners, blowing agents may also be present. Preservatives may also be used. The cleaning compositions may also contain lime-dissolving components, preferably free citric acid. By virtue of the above-described properties of the hydroxycarboxylic acids used in accordance with the invention, the presence of other complexing agents, particularly for calcium ions, is not preferred and is preferably ruled out. Preferred applications for the present technical teaching are in the field of hard surface cleaners, preferably toilet cleaners, the hydroxycarboxylic acids preferably being used in liquid or gel-form cleaners. The hydroxycarboxylic acids are also preferably used in foam cleaners and in so-called air fresheners, i.e. water-based preparations for perfuming air. However, perfume oils and the solubilizer may also be stored separately from one another and mixed just before use, for example in a suitable dosing unit.

If the esters according to the invention are formulated with other ingredients to make an end product, it is important to ensure that the pH of that end product is in the range from 4 to 7 and preferably 4.5 to 6.5. In addition, the ethoxylated or alkoxylated esters according to the invention are preferably used together with perfume oils in a ratio by weight which should preferably be between 10:1 and 1:1. Perfume oils may be used in a quantity of at most 60% by weight, based on the quantity of ester according to the invention used.

EXAMPLES

I. Production of the Esters

1. Production of an ester according to the invention from citric acid and a $C_{12-18}$ fatty alcohol+7 EO:

In a stirred reactor, 28.05 kg (0.146 mol) water-free citric acid and 75.16 kg (0.146 Kmol) Dehydol LT 7™, a product of Cognis Deutschland GmbH & Co. KG (a fatty alcohol mixture ethoxylated with 7 mol ethylene oxide having the following chain distribution in % by weight: <C12:0-3%; C12: 48-58%; C14: 18-24%; C16: 8-12%; C18: 11-15%; >C18: 0-1%), were heated under nitrogen to 160° C. and stirred at that temperature until the theoretical quantity of water had been released (5.5 hours). A light yellow, clear and liquid product with the following characteristics was obtained: saponification value (DIN): 222, acid value (DIN): 132, free citric acid: 2.8% by weight.

2. Another citric acid ester was produced in the same way as in Example 1. The fatty alcohol Dehydol® LT 7 was replaced by an equimolar quantity of a fatty alcohol mixture based on $C_{10}/C_{16}$ fatty alcohols which had been reacted with 1.2 parts propylene oxide (PO) and 6.4 parts ethylene oxide (EO) per part fatty alcohol. A light yellow, clear and liquid product with the following characteristic data was obtained: acid value 166, saponification value 243.

II. Performance Tests

1. In order to test the effect according to the invention, a 10% by weight aqueous solution of various surfactants was prepared. To this end, the surfactant was first mixed with the perfume oil and water was then added. The higher the percentage content of perfume oil, the better the solubilizing effect of the surfactant. In Table 1 below, V stands for known products and E for alkoxylated esters according to the invention.

Examples E1 and E2 according to the invention use a citric acid ester as described in I.1 or I.2.

TABLE 1

| No. | Surfactant | Perfume oil | Quantity (% by wt.) before clouding |
|---|---|---|---|
| V1a | 2-Hydroxy-$C_{12}$-(PO)$_1$-(EO)$_9$-glycol ether | Orange oil | 4 |
| V1b | 2-Hydroxy-$C_{12}$-(PO)$_1$-(EO)$_9$-glycol ether | Lemon oil terpene | 4 |
| V1c | 2-Hydroxy-$C_{12}$-(PO)$_1$-(EO)$_9$-glycol ether | Octyl aldehyde | 2 |
| V2a | Hydrogenated castor oil with 40 parts ethylene oxide (EO) | Orange oil | 4 |
| V2c | Hydrogenated castor oil with 40 parts ethylene oxide (EO) | Octyl aldehyde | 4 |
| V3a | Mixture of $C_{12-18}$ fatty alcohol + 7EO, $C_{8-10}$ APG and sodium lauryl ether sulfate + 2EO corresponding to the disclosure of EP 1441024 | Orange oil | 3 |
| V3b | Mixture of $C_{12-18}$ fatty alcohol + 7EO, $C_{8-10}$ APG and sodium lauryl ether sulfate + 2EO corresponding to the disclosure of EP 1441024 | Lemon oil terpene | 3 |
| E1a | Ester of lauryl citrate and $C_{12-18}$ fatty alcohol + 7EO | Orange oil | 6 |
| E1b | Ester of lauryl citrate and $C_{12-18}$ fatty alcohol + 7EO | Lemon oil terpene | 5 |
| E1c | Ester of lauryl citrate and $C_{12-18}$ fatty alcohol + 7EO | Octyl aldehyde | 9.5 |
| E2a | Ester of $C_{10/16}$ fatty alcohol with 1.2 parts PO and 6.4 parts EO | Orange oil | 9.5 |
| E2b | Ester of $C_{10/16}$ fatty alcohol with 1.2 parts PO and 6.4 parts EO | Lemon oil terpene | 9.5 |
| E2c | Ester of $C_{10/16}$ fatty alcohol with 1.2 parts PO and 6.4 parts EO | Octyl aldehyde | 7.5 |

Examples E1 and E2 according to the invention show a distinctly higher percentage of dissolved perfume oil than the known solubilizers C1 to C3.

What is claimed is:

1. A process for solubilizing perfumes in water, comprising combining
    (i) one or more perfumes which are 1% or less soluble in water and are liquid at room temperature,
    (ii) one or more esters of hydroxycarboxylic acids with alkoxylated fatty alcohols wherein the hydroxycarboxylic acid is selected from the group consisting of citric acid, lactic acid, malic acid, tartaric acid, gluconic acid and mixtures thereof and the alkoxylated fatty alcohols correspond to the general formula (I):

$$R\text{-}O\text{-}(C_3H_6O)_m(C_2H_4\text{-}O\text{-})_n\text{-}H \qquad (I)$$

in which m stands for 0, 1 or 2 and n stands for 1 to 10, and the substituent R is a saturated, unsaturated, branched or unbranched $C_{8-22}$ alkyl group,
    wherein the resulting hydroxycarboxylic acid ester contains a free carboxylic acid or salt thereof, and
    (iii) water,
    wherein the combination contains less than 5%, based on total weight, of the free hydroxycarboxylic acid, and
    wherein the ratio of the one or more alkoxylated esters of hydroxycarboxylic acids (ii) to the one or more perfumes (i) is from 2:1 to 1:1.

2. The process of claim 1 wherein citric acid is selected as the hydroxycarboxylic acid component.

3. The process of claim 1 wherein the alkoxylated fatty alcohols correspond to formula (I) where m is 0 and n is a number from 2 to 8.

4. The process of claim 1 wherein R in formula (I) represents saturated, unbranched alkyl groups containing 12 to 18 carbon atoms.

5. The process of claim 1 wherein the perfume is selected from orange oil, lemon oil terpene and mixtures thereof.

6. The process according to claim 1 wherein the perfume is octyl aldehyde.

7. The process according to claim 1 wherein the perfume is cumene.

8. The process of claim 1 wherein the free carboxylic acid is in the form of an alkali metal, alkaline earth metal, ammonium, alkylammonium, alkylammonium or glucammonium salt.

9. The process of claim 1 wherein the hydroxycarboxylic acid esters are polyesters comprising 75 to 95% monoesters and 5 to 25% diesters, by weight.

10. The process according to claim 1 wherein the one or more esters of hydroxycarboxylic acids are selected from citric acid ester mixtures of ethoxylated alcohols of general formula (I), where R is a linear alkyl group derived from a fatty alcohol mixture containing 45 to 75% by weight C12 alcohol, 15 to 35% by weight C14 alcohol, 0 to 15% by weight C16 alcohol and 0 to 20% by weight C18 alcohol and n is a number of 5 to 9, with the proviso that the ratio by weight of monoester to diester in the citric acid ester mixtures is in the range from 10:1 to 3:1.

11. The process of claim 1, wherein the combination contains no free hydroxycarboxylic acid.

12. The process of claim 1, wherein the one or more perfumes comprise 5 to 9.5% by weight, based on the total weight of the combination.

13. The process of claim 1, wherein the ratio of the one or more alkoxylated esters of hydroxycarboxylic acids (ii) to the one or more perfumes (i) is from 4:1 to 1:1.

\* \* \* \* \*